United States Patent [19]

Venero et al.

[11] Patent Number: 4,584,372

[45] Date of Patent: Apr. 22, 1986

[54] COMPOUND 3-(1,2,3,6-TETRAHYDRO-1,3-DIMETHYL-2,6-DIOXOPURINE-7-ACETYL-8-(2-PHENYLE-THYL)-1-OXA-3,8-DIAZASPIRO-(4,5)DECAN-2-ONE AND A PROCESS OF PREPARATION THEREOF

[76] Inventors: Aurelio O. Venero, S. Bartolome, 12 - 3° C.; Ramon M. Pestana, Iparraguirre, 20 - 7° A., both of Lejona (Vizcaya), Spain

[21] Appl. No.: 552,481

[22] Filed: Nov. 16, 1983

[30] Foreign Application Priority Data

Nov. 23, 1982 [ES] Spain ................................. 517622

[51] Int. Cl.$^4$ ............................................ C07D 473/28
[52] U.S. Cl. .................................... 544/230; 544/264; 544/265; 544/267; 544/268; 544/269; 544/271; 546/19
[58] Field of Search ............... 544/264, 265, 267, 268, 544/269, 271, 230

[56] References Cited

U.S. PATENT DOCUMENTS 3,935,196  1/1976  Higuchi ........................... 544/271

FOREIGN PATENT DOCUMENTS 1509409  5/1978  United Kingdom .

OTHER PUBLICATIONS

Lespagnol et al., Annales Pharmaceutiques Francaises, 1974, No. 3–4, pp. 237–240.
Lafarquim, Span. 423,809, Chemical Abstracts 86:89898v.
FAES, Span. 509245, Chemical Abstracts 99:105054t.

Primary Examiner—Donald G. Daus
Assistant Examiner—Robert Benson
Attorney, Agent, or Firm—Bucknam and Archer

[57] ABSTRACT

The new compound 3-(1,2,3,6-tetrahydro-1,3-dimethyl-2,6-Dioxopurine-7-acetyl-8-(2-phenylethyl)-1-oxa-3,8-diazaspiro-(4,5)decan-2-one and the process of preparation are described.

2 Claims, No Drawings

COMPOUND 3-(1,2,3,6-TETRAHYDRO-1,3-DIMETHYL-2,6-DIOXOPURINE-7-ACETYL-8-(2-PHENYLETHYL)-1-OXA-3,8-DIAZASPIRO-(4,5)DECAN-2-ONE AND A PROCESS OF PREPARATION THEREOF

BACKGROUND OF THE INVENTION

The present invention relates to the preparation of a new derivative of 8-(2-phenylethyl)-1-oxa-3,8-diazaspiro-(4.5) decan 2-one, by reaction of this compound, or an appropriate salt thereof, with 1,2,3,6-tetrahydro-1,3-dimethyl-2,6-dioxopurine-7-acetic acid, or suitable derivative in the conditions stated hereinafter.

As reagent derivatives of the acid may be used its halides, preferably chloride and bromide, which result in good yields and are prepared, by means of known processes described in the scientific literature, by reaction of the acid with the corresponding phosphorus halides or thionyl halides. Acid anhydride is also used to carry out the reaction, which may be prepared "in situ", although the yield of the process may require recovery of the acid, which is formed as a secondary product at a ratio of one mol of acid to one mol of 1,2,3,6-tetrahydro-1,3-dimethyl-2,6-dioxopurine-7-acetic anhydride, which is rather laborious.

As a medium is used an organic solvent or a mixture of two or more organic solvents which are inert in contrast to the reagents used, and which are selected among the terciary amines, preferably pyridine, trialkylamines and N-methyl morpholine, the aromatic hydrocarbons, preferably benzene, toluene and xylene, the halogenated carbons, preferably chloroform, dichloromethane, trichloroethane and dichloroethane, and the N,N-dialkylamides, preferably N,N-dimethyl formamide and N,N-dimethyl acetamide. Moisture must be avoided to the maximum, since it would affect negatively in the reaction, and this fact causes those solvents in which water is present to dry up, thereby reducing their content by physical and/or chemical means.

On the other hand, the temperature at which said reaction is carried out must be adequately controlled, which in no case should exceed 150° C., since it would result in a form different from the desired one, and the quality of the product would be inferior to that obtained in operating between 50° and 130° C.

The reaction product may be isolated in the form of free base or in the form of an acceptable pharmaceutical salt, considering as such those of mineral acids, such as hydrocloric acid and sulfuric acid, and organic acids, such as acetic acid, 7-theophylline acid, lactic acid, oxalic acid, maleic acid and thenoic acid.

The 3-(1,2,3,6-tetrahydro-1,3-dimethyl-2,6-dioxopurine-7-acetyl)-8-(2-phenyl ethyl)-1-oxa-3,8-diazaspiro (4.5) decan-2-one and its acceptable pharmaceutical salts referred to by the present invention offer bronchodilatory activity, both "in vitro" and "in vivo", as well as anti-inflammatory activity, which make them potentially useful for their use as drugs.

The following examples are presented merely as an illustration and should not be interpreted as limiting the present invention, since many variants thereof are possible, without departing from the spirit and scope of the invention.

EXAMPLE 1

In a reactor of 250 liters provided with heating, coolant for backflow, agitation and system for distillation with vacuum, are introduced 12 Kgs. of 1,2,3,6-tetrahydro-1,3-dimethyl-2,6-dioxopurine-7-acetic acid and 100 liters of thionyl chloride. The mixture is made to reflux for one hour and at the end of said time the thionyl chloride excess is distilled at reduced pressure. To the residue are added 100 liters of dry benzene, which is heated close to the boiling point and the solution is transferred to an enameled vat, passing it first through a clarifying filter with heating liner. After allowing it to settle for 24 hours, crystals are obtained, which are separated by filtration and dried. The weight of the dry product is 4.7 Kg. and its melting point 150–4° C.

In the same reactor previously used, once clean and dry, are introduced 150 liters of a mixture of dry pyridine and benzene, and to this are added the 4.7 kg. of acid chloride and 4.5 kg. of 8-(2-phenyl ethyl)-1-oxa-3,8-diazaspiro (4.5) decan-2-one, shaking it energetically and heating it to boiling point. When all of the acid chloride has reacted, most of the solvent is distilled and the residue is poured on cold methanol, shaking it. The solid deposited is separated by filtration, it is washed with water, drained and is immediately crystallized with acetone. The crystals formed are separated by filtration and dried in an oven. In this manner is obtained the 3-(1,2,3,6-tetrahydro-1,3-dimethyl-2,6-dioxopurine-7-acetyl)-8-(2-phenyl ethyl)-1-oxa-3,8-diazaspiro (4.5) decan-2-one which contains 4% water and presents a melting point of 96° C.

EXAMPLE 2

In a reactor with a capacity of 200 liters, provided with agitation, coolant for flowback and oil bath, are introduced 150 liters of xylene, to which are later added 25 kg. of 8-(2-phenyl ethyl)-1-oxa-3,8-diazaspiro (4.5) decan-2-one. In various portions are added 25 kg. of the 1,2,3,6-tetrahydro-1, 3-dimethyl-2,6-dioxopurine-7-acetic acid chloride, prepared according to the process of C. Fulvio and col. (Ann. Chim. (Rome), 45, 983 (1955). The reaction mixture is heated for 30 hours and then is allowed to cool slowly, thereby forming chlorhydrate crystals of the 3-(1,2,3,6-tetrahydro-1,3-dimethyl-2,6-dioxopurine-7-acetyl)-8-(2-phenylethyl)-1-oxa-3,8-diazaspiro (4.5) decan-2-one which are separated by filtration, washed with acetone and dried in an oven. The product melts at 293–5° C. and its IR and RMN spectra and elemental analysis conform to its chemical structure.

What is claimed is:

1. The compound 3-(1,2,3,6-tetrahydro-1,3-dimethyl-2,6-dioxopurine-7-acetyl)-8-(2-phenylethyl)-1-oxa-3,8-diazaspiro (4.5) decan-2-one or a pharmaceutically acceptable salt thereof.

2. The compound according to claim 1 wherein the salt is the hydrochloride, the lactate, maleate, sulfate, oxalate or thenoate.

* * * * *